United States Patent [19]

Chen et al.

[11] Patent Number: 5,189,214
[45] Date of Patent: Feb. 23, 1993

[54] PRODUCTION OF ACETIC ACID

[75] Inventors: S. C. Chen, Taipei; C. C. Chu, Kaohsiung; F. S. Lin, Kaohsiung; F. J. Huang, Kaohsiung, all of Taiwan

[73] Assignees: Dairen Chemical Corp.; Chang Chun Petrochemical Co., Ltd., Taipei, Taiwan

[21] Appl. No.: 745,349

[22] Filed: Aug. 15, 1991

[51] Int. Cl.$^5$ ............................................. C07C 51/12
[52] U.S. Cl. ..................................... 562/519; 562/517
[58] Field of Search ................................ 562/519, 517

[56] References Cited

U.S. PATENT DOCUMENTS 4,659,518  4/1987  Rizkalla .............................. 260/413

Primary Examiner—Arthur C. Prescott
Attorney, Agent, or Firm—Sachs & Sachs

[57] ABSTRACT

A process of preparing acetic acid by reacting a mixture of a methyl ester, an alcohol, and water preferably as a solution in aqueous acetic acid, with carbon monoxide, with or without hydrogen, at a selected partial pressure, in the presence of a catalyst, preferably composed of a nickel or nickel/molybdenum compound with phosphorus compounds as ligands, and a promoter composed of iodine compounds, at a predetermined temperature is disclosed.

6 Claims, No Drawings

PRODUCTION OF ACETIC ACID

BACKGROUND OF THE INVENTION

1. Field of the Invention

This invention relates to production of acetic acid, by reaction of a feedstock of a methyl ester, methanol and water, with carbon monoxide, at a predetermined pressure and temperature, in the presence of a suitable catalyst.

2 Description of the Prior Art

Acetic acid may be prepared from a feedstock containing methyl esters by a process which involves three steps. This process requires acid hydrolysis of a methyl ester such as methyl acetate into acetic acid and methanol, followed by separation of methanol and water by distillation, and subsequent carbonylation of the separated methanol with carbon monoxide to form additional acetic acid. However, the process is uneconomical because the high latent heats of vaporization of both water and methanol requires large quantities of steam and cooling water during the separation step.

U.S. Pat. No. 3,769,329 issued to Frank E. Paulik, et al disclosed a process for preparation of acetic acid by the carbonylation reaction of an alcohol, ester, or ether with carbon monoxide in the presence of a rhodium catalyst. In that process the reaction mixture is flash boiled to recover the crude product from the catalyst. However, such a rhodium catalyst will form inactive precipitates of rhodium compounds under a low carbon monoxide partial pressure and high temperature and the reaction rate decreases. As such, the flash boiling step may only be carried out at lower temperatures. This in turn results in a lower concentration of acetic acid in the crude product and then large quantities of steam and cooling water are required in the purification operations. Meanwhile, since rhodium is an expensive precious metal, the overall production cost of the acid is high.

Furthermore, in the above prior art if the concentration of the methyl compound e.g., methyl iodide, methanol, or methyl acetate, is too high, the catalyst loses its activity; and if the water concentration is too low or the carbon monoxide partial pressure is too low the rhodium catalyst precipitates. Thus the window of operation conditions in that invention is narrow and the control is difficult.

Naglieri, in U.S. Pat. No. 4,356,320, disclosed an improved carbonylation process for the production of acetic acid using less expensive nickel, or a nickel compound, in place of rhodium. However, the new process still required methanol feedstock as the source of the methanol reactant in the carbonylation process.

Accordingly, it is an object of this invention to provide a new process for the industrial production of acetic acid.

Another object of the invention is to provide a process for making acetic acid which uses a feedstock of a methyl ester, water and an alcohol.

Among the other objects of the invention is to provide a carbonylation process for the production of acetic acid using a catalyst of nickel or a nickel compound, with or without molybdenum, containing phosphorus compounds as ligands, and an iodine promoter.

Yet another object of the invention is to provide a process for the production of acetic acid in which the catalyst remains in a dissolved state and active while carrying out the step of recovery of the acetic acid from the reaction product, at high temperatures and low carbon monoxide partial pressures.

These and other objects of the invention will be made apparent from the following description hereinafter.

SUMMARY OF THE INVENTION

The present invention is related to a process of preparing acetic acid by reacting a mixture of a methyl ester, an alcohol, and water, preferably as a solution in aqueous acetic acid, with carbon monoxide, with hydrogen, at a selected partial pressure, in the presence of a catalyst, preferably composed of nickel or a nickel compound, with or without molybdenum, with phosphorus compounds as ligands, and a promoter composed of iodine compounds, at a predetermined temperature.

DETAILED DESCRIPTION OF THE INVENTION

In accordance with the present invention, there is provided a process for the production of acetic acid by catalytic reaction with carbon monoxide of a reactant feedstock. As a feature of the invention, the reactant feedstock in the process herein is a mixture of methyl acetate, optionally with methyl formate, methanol and water. The molar ratio of water to methyl acetate present in the reaction feedstock mixture must be at least 1:1 to enable an acid hydrolysis reaction to occur and maintain mass balance in the reaction system. Excess water in the feedstock will function in the process as a solvent in the reaction system.

The carbon monoxide reactant in the process is maintained at a partial pressure between about 20 and 80 $kg/cm^2$, preferably about 30 and 50 $kg/cm^2$. The hydrogen in the process is maintained at a partial pressure between about 1 and 20 $kg/cm^2$, preferably about 1.5 and 13 $kg/cm^2$.

The catalyst in the process of the present invention may be any catalyst suitable for carbonylation reactions. This catalyst comprises nickel or a nickel compound, organic or inorganic, with or without molybdenum, which is effective to introduce catalyst into the reaction system. Suitable and typical nickel and molybdenum compounds include the carbonate, oxide, hydroxide, bromide, iodide, chloride, oxyhalide, hydride, lower alkoxide (methoxide), phenoxide or carboxylates, where the carboxylate ion is derived from an alkanoic acid of 1 to 20 carbon atoms such as acetates, butyrates, decanoates, laurates, benzoates, and the like Similarly, complexes of nickel and molybdenum can be employed, for example, metal carbonyls and metal alkyls as well as chelates, association compounds and enol salts. Examples of other complexes include bis-(triphenyl phosphine) nickel dicarbonyl, tricyclopentadienyl trinickel dicarbonyl, and tetrakis (triphenyl phosphate) nickel and corresponding complexes of molybdenum.

A most preferred catalyst system includes a nickel compound such as nickel iodide, a molybdenum compound such as molybdenum hexacarbonyl, and a phosphorus compound which will coordinate with the nickel or molybdenum compound to form active complexes. Suitably such phosphorus compounds include trivalent phosphorus compounds such as phosphines, e.g., triphenyl phosphine, triisobutyl phosphine and tributyl phosphine. Generally the atomic ratio of phosphorus atoms to nickel atoms in such complexes range from about 2:1 to 10:1, preferably about 3:1 to 7:1. Although usually the phosphorus compound is added separately to the catalyst system, it is also possible to add it as a complex with the nickel or molybdenum or both, as described above.

While this invention may be practiced with nickel or its complexes of phosphorous compound coordination alone, however if molybdenum or its same compound are added to the above catalyst, the life of the catalyst is prolonged and the reaction rate increased.

The catalyst system also includes an iodine promoter which is typically an iodide present as a hydrocarbonyl iodide, another organic iodide, the hydroiodide or other inorganic iodide, e.g. a salt, such as the alkali metal or other metal salt. Accordingly, suitable iodine promoters include methyl iodide, lithium iodide and hydrogen iodide. Generally the iodine promoter is added at a level of about 8 and 15 wt % iodine atoms based on the total weight of the reactant mixture. In this range, the desired reaction rate for the carbonylation is maintained during the process. Make-up iodide may be added to keep the iodide concentration within this range, if necessary.

The reaction temperature is generally maintained between about 180 and 220 degrees C.; preferably about 200 and 210 degrees C., thereby assuring a rapid reaction rate between the feedstock and carbon monoxide without causing corrosion of the reactor.

Methanol in the feed stream may or may not be the primary reactant source for the carbonylation reaction. Suitable molar ratio of methyl ester to methanol in the reactant mixture may vary very widely, usually from 1:99 to 99:1.

The process of the invention may be carried out in a continuous, semi-continuous or in a batch manner, as desired.

The process of the invention may be carried out in a continuous, semi continuous or in a batch manner, as desired.

The catalyst is included in the reaction mixture in an amount which provides a concentration of nickel atom or molybdenum atom between about 0.2 and 1.0 wt %, and preferably between about 0.4 and 0.8 wt %, based on the total weight content of the reaction mixture. The use of these concentration ranges assure that the nickel or nickel/molybdenum catalyst will remain in solution during the process.

After a suitable residence time the final reaction mixture is separated into its several constituents, as by distillation. As a feature of this invention, the nickel or nickel/molybdenum catalyst remains in a dissolved condition at the high operating temperatures and low carbon monoxide partial pressures present during the distillation step. Accordingly, in this process the separation step will afford the desired crude acetic acid product in high yield without excessive consumption of steam and cooling water. The unreacted alcohol, ester and water may be recycled and reused as reactants after separation by distillation.

Conversion, C, in %, of the methyl ester and methanol in the feedstock into acetic acid is defined as follows:

$$C = \frac{A - B}{A} \times 100\%$$

methyl ester and methanol present after completion of the reaction.

The invention will now be illustrated by the following examples, which show the effect of different reaction conditions upon conversion, and in which the initial weight of the reaction mixture is 600 g, the total number of moles of methyl acetate, methyl formate and methanol present is 4.

EXAMPLE 1

A charge of nickel iodide 26.0g (0.0612 mole, nickel content 0.6 wt %), triphenyl phosphine 32.1 g (0.245 mole, P/Ni molar ratio 4/1), methyl iodide 80.5g (0.567 mole, iodine content 12 wt %), water 24.000g (1.333 moles, 4 wt %), acetic acid 142.4g (2.371 mole, 23.7 wt %), and a reactant feed mixture of methyl acetate/methyl formate/methanol/water in a molar ratio of 60/20/20/60, 294.8g (methyl acetate 178g, 2.4 mole; methyl formate 48.0g, 0.8 mole; methanol 25.6g, 0.8 mole; water 43.2g, 2.4 mole) are introduced into a 1 liter pressure reactor equipped with an agitator. After purging with carbon monoxide, the reaction system is heated under agitation. When the temperature reaches 210 degrees C. the partial pressure of carbon monoxide is increased to start the reaction. During the reaction, the carbon monoxide partial pressure is maintained at 30kg/cm$^2$, and the hydrogen partial pressure is maintained at 5kg/cm$^2$. After 1.5 hours of reaction, the pressure is released and the reaction system is cooled.

The product is analyzed by gas chromatography (Hewlett Packard model 5840A) with 1,4-dioxane as an internal standard through a column packed with PEG 6,000 on Celite. The analysis shows a residual methyl acetate of only 0.22 mole, methyl formate 0.05 mole, and methanol 0.01 mole. The conversion is:

$$C = \frac{(2.4 + 0.8 + 0.8) - (0.22 + 0.05 + 0.01)}{(2.4 + 0.8 + 0.8)} \times 100\% = 93.50\%$$

EXAMPLE 2

The procedure of Example 1 is followed except that the reactant mixture is methyl acetate/methyl formate/methanol/water in a molar ratio of 80/19/1/80, 341.5g (methyl acetate 237g, 3.2 mole; methyl formate 45.6g, 0.76 mole; methanol 1.28g, 0.04 mole; water 57.6g, 3.2 mole) and acetic acid is 95.7g (i.e. the total weight of the charge at the beginning the reaction starts is 600g). Residual methyl acetate is 0.24 mole, methyl formate 0.04 mole, and methanol 0.01 mole. Conversion is 92.75%.

EXAMPLE 3

The procedure of Example 1 is followed except that the reactant mixture of methyl acetate/methanol/water is present in a molar ratio of 1/99/1 130.7g (methyl acetate 2.96g, 0.04 mole; methanol 127g, 3.96 mole; water 0.72g, 0.04 mole) and acetic acid is 306.5g. The analysis shows a residual methyl acetate of 0.26 mole and methanol 0.02 mole. Conversion is 93.00%.

SUMMARY OF EXAMPLES 1 THROUGH 3

TABLE 1

| Example | Molar Ratio of Methyl Ester/Methanol in the Feed | Conversion (%) |
| --- | --- | --- |
| 1 | 80/20 | 93.50 |
| 2 | 99/1 | 92.75 |
| 3 | 1/99 | 93.00 |

These results demonstrate that a variation of the molar ratio of methyl ester to methanol in the feed from 1/99 to 99/1 had no effect on conversion.

EXAMPLE 4

The procedure of Example 3 is followed except that 129.4g of a feed mixture of reactants: methyl formate and methanol, in a molar ratio of 1/99 (methyl formate 2.40g, 0.04 mole; methanol 127g. 3.96 mole), and acetic acid, 307.8g, are charged. The residual methyl acetate is 0.24 mole, methyl formate is 0.01 mole, and methanol 0.02 mole. Conversion is 93.25%.

EXAMPLE 5

The procedure of Example 1 is followed except that nickel iodide 43.3g (0.102 mole, nickel content 1.0 wt %), triphenyl phosphine 26.7g (0.204 mole, P/Ni molar ratio 2/1), and acetic acid 130.5g are charged. Residual methyl acetate is 0.26 mole, methyl formate 0.02 mole, and methanol 0.03 mole. Conversion is 92.25%.

EXAMPLE 6

The procedure of Example 1 is followed except that triphenyl phosphine 80.2g (0.612 mole, P/Ni molar ratio 10/1), and acetic acid 94.3g are charged, and a carbon monoxide partial pressure of 80 kg/cm$^2$ is used. The residual methyl acetate is 0.21 mole, methyl formate of 0.01 mole, and methanol 0.02 mole. Conversion is 94.00%.

EXAMPLE 7

Example 1 is followed except that methyl iodide 134g (0.946 mole, iodine content 20 wt %), and acetic acid 88.9g are charged. The reaction temperature is 180 degrees C. The residual methyl acetate is 0.23 mole, methyl formate 0.02 mole, and methanol 0.04 mole. Conversion is 92.75%.

EXAMPLE 8

Example 1 is followed except that methyl iodide 33.6g (0.236 mole, iodine content 5 wt %), and acetic acid 189.3g are charged. The residual methyl acetate is 0.30 mole, methyl formate 0.04 mole, and methanol 0.05 mole. Conversion is 90.25%.

EXAMPLE 9

Example 1 is followed except that the reaction temperature is 220 degrees C., and a carbon monoxide partial pressure of 20 kg/cm$^2$ and hydrogen partial pressure of 1 kg/cm are used. The residual methyl acetate is 0.06 mole, methyl formate 0.01 mole, and methanol 0.02 mole. Conversion is 97.75%.

EXAMPLE 10

A charge of nickel iodide 26.0g (0.0612 mole, nickel content 0.6 wt %), molybdenum trioxide 5.87g (0.0408 mole, molybdenum content 0.65 wt %), triphenyl phosphine 32.1 g (0.245 mole, P/Ni molar ratio 4/1), methyl iodide 80.5g (0.567 mole, iodine content 12 wt %), water 24.0g (1.33 moles, 4 wt %), acetic acid 136.7g (2.28 moles, 22.8 wt %), and a reactant feed mixture of methyl acetate/methyl formate/methanol/water in a molar ratio of 60/20/20/60, 294.8g (methyl acetate 178g, 2.4 moles; methyl formate 48.0g, 0.8 mole, methanol 25.6g, 0.8 mole; water 43.2g, 2.4 moles) are introduced into a 1 liter pressure reactor equipped with an agitator. After purging with carbon monoxide, the reaction system is heated under agitation. When the temperature reaches 210 degrees C. the partial pressure of carbon monoxide and hydrogen is increased to start the reaction. During the reaction, the carbon monoxide partial pressure is maintained at 30 kg/cm$^2$, the hydrogen partial pressure is maintained at 5 kg/cm$^2$. After 1.0 hour of reaction, the pressure is released and the reaction system is cooled.

The product is analyzed in a way similar to that in Example 1. The analysis shows a residual methyl acetate of only 0.24 mole, methyl formate 0.07 mole, and methanol 0.03 mole. The conversion is:

$$C = \frac{(2.4 + 0.8 + 0.8) - (0.24 + 0.07 + 0.03)}{(2.4 + 0.8 + 0.8)} \times 100\% = 91.50\%$$

EXAMPLE 11

The procedure of Example 10 is followed except that the reactant mixture is methyl acetate/methyl formate/methanol/water in a molar ratio of 80/19/1/80, 342.2g (methyl acetate 237g, 3.2 moles; methyl formate 45.6g, 0.76 mole; methanol 1.28g, 0.04 mole; water 57 6g, 3.2 moles) and acetic acid is 89.3g (i.e. the total weight of the charge at the beginning the reaction starts is 600g). Residual methyl acetate is 0.32 mole, methyl formate 0.01 mole, and methanol trace. Conversion is 91.75%.

EXAMPLE 12

The procedure of Example 10 is followed except that the reactant mixture of methyl acetate/methanol/water is present in a molar ratio of 1/99/1 130.7g (methyl acetate 2.96g, 0.04 mole; methanol 127g, 3.96 moles; water 0.720g, 0.04 mole) and acetic acid is 300.8g. The analysis shows a residual methyl acetate of 0.29 mole and methanol 0.03 mole. Conversion is 92.00%

SUMMARY OF EXAMPLES 10 THROUGH 12

TABLE 2

| Example | Molar Ratio of Methyl Ester/Methanol in the Feed | Conversion (%) |
|---|---|---|
| 10 | 80/20 | 91.50 |
| 11 | 99/1 | 91.75 |
| 12 | 1/99 | 92.00 |

These results demonstrate that a variation of the molar ratio of methyl ester to methanol in the feed from 1/99 to 99/1 had no effect on conversion.

EXAMPLE 13

The procedure of Example 12 is followed except that 129.4g of a feed mixture of reactants: methyl formate and methanol, in a molar ratio of 1/99 (methyl formate 2.40g, 0.04 mole; methanol 127g, 3.96 moles), and acetic acid, 302.1 g are charged. The residual methyl acetate is 0.31 mole, methyl formate is 0.01 mole, and methanol 0.03 mole. Conversion is 91.25%.

EXAMPLE 14

The procedure of Example 10 is followed except that nickel iodide 43.3g (0.102 mole, nickel content 1.0 wt %), molybdenum trioxide 9.79g (0.0680 mole, molybdenum content 1.09 wt %), triphenyl phosphine 26.7g (0.204 mole, P/Ni molar ratio 2/1), and acetic acid 120.9g are charged. Residual methyl acetate is 0.28 mole, methyl formate 0.03 mole, and methanol 0.03 mole. Conversion is 91.50%.

EXAMPLE 15

The procedure of Example 10 is followed except that triphenyl phosphine 80.2g (0.612 mole, P/Ni molar ratio 10/1), and acetic acid 88.6g are charged, and a carbon monoxide partial pressure of 80 kg/cm$^2$ and a hydrogen partial pressure of 20 kg/cm2 are used. The residual methyl acetate is 0.24 mole, methyl formate is 0.02 mole, and methanol 0.02 mole. Conversion is 93.0%.

EXAMPLE 16

Example 10 is followed except that methyl iodide 134g (0.946 mole, iodine content 20 wt %) and acetic acid 83.2g are charged. The reaction temperature is 180 degrees C. The residual methyl acetate is 0.30 mole, methyl formate 0.05 mole, and methanol 0.05 mole Conversion is 90.0%.

EXAMPLE 17

Example 10 is followed except that methyl iodide 33.6g (0.236 mole, iodine content 5 wt %), and acetic acid 183.6g are charged, the residual methyl acetate is 0.29 mole, methyl formate 0.06 mole, and methanol 0.05 mole. Conversion is 90.0%.

EXAMPLE 18

Example 10 is followed except that the reaction temperature is 220 degrees C, and a carbon monoxide partial pressure of 20 kg/cm$^2$ and a hydrogen partial pressure of 1 kg/cm$^2$ are used. The residual methyl acetate is 0.29 mole, methyl formate 0.03 mole, methanol 0.04 mole. Conversion is 91.00%

What is claimed is:

1. A process for the production of acetic acid which comprises reacting a feedstock which includes a mixture of methyl acetate and methyl formate, methanol and water, with carbon monoxide, in the presence of a catalyst, at a predetermined temperature and pressure, wherein said water and said methyl esters are present in the feedstock in a molar ratio of at least 1:1, respectively, the partial pressure of the carbon monoxide reactant during the process is between 20 and 80 kg/cm$^2$, ad , wherein said methyl acetate and methyl formate reactants are substantially consumed during the process.

2. A process according to claim 1 wherein said catalyst is nickel or a nickel compound with or without molybdenum, containing phosphine ligands and an iodide promoter.

3. A process according to claim 2 wherein excess water, if present, is a solvent in the reaction system.

4. A process according to claim 2 wherein iodine is present in the feedstock.

5. A process according to claim 1 wherein the reaction temperature is maintained between 180 and 220 degrees C.

6. A process according to claim 1 wherein the reactant feed mixture includes methanol at a molar ratio of methyl ester to methanol of between 99:1 to 1:99.

* * * * *